United States Patent
Ohkawa

(10) Patent No.: US 8,440,726 B2
(45) Date of Patent: May 14, 2013

(54) SOLUBILIZING COMPOSITION

(75) Inventor: Yusuke Ohkawa, Kanagawa (JP)

(73) Assignee: NOF Corporation, Tokyo (JP)

( * ) Notice: Subject to any disclaimer, the term of this patent is extended or adjusted under 35 U.S.C. 154(b) by 1353 days.

(21) Appl. No.: 12/059,029

(22) Filed: Mar. 31, 2008

(65) Prior Publication Data

US 2008/0249191 A1    Oct. 9, 2008

(30) Foreign Application Priority Data

Mar. 30, 2007  (JP) ................................ 2007-094575

(51) Int. Cl.
*A61K 47/12*   (2006.01)

(52) U.S. Cl.
USPC ........................... 514/784; 514/937; 424/450

(58) Field of Classification Search ................. 514/784, 514/211, 937; 424/450
See application file for complete search history.

(56) References Cited

U.S. PATENT DOCUMENTS

| | | | |
|---|---|---|---|
| 5,658,898 A | | 8/1997 | Weder et al. |
| 5,814,321 A | * | 9/1998 | Miyahara et al. .......... 424/278.1 |
| 6,008,192 A | | 12/1999 | Al-Razzak et al. |
| 6,235,282 B1 | * | 5/2001 | Riviere et al. .............. 424/184.1 |
| 6,383,471 B1 | * | 5/2002 | Chen et al. ...................... 424/45 |
| 2003/0185878 A1 | * | 10/2003 | Hoshino et al. ............... 424/450 |
| 2006/0104999 A1 | | 5/2006 | Chung et al. |

FOREIGN PATENT DOCUMENTS

| | | |
|---|---|---|
| JP | 2001-122779 A | 5/2001 |
| JP | 2001-151669 A | 6/2001 |
| JP | 2001-516351 A | 9/2001 |
| JP | 2005-538090 A | 12/2005 |
| JP | 2006-248928 A | 9/2006 |
| WO | 97/36611 A1 | 10/1997 |
| WO | WO 97/36611 * | 10/1997 |
| WO | 03/066025 A1 | 8/2003 |

OTHER PUBLICATIONS

Japanese Office Action issued in corresponding Japanese Patent Application No. 2007-094575 on Jul. 18, 2012.

* cited by examiner

*Primary Examiner* — Fereydoun G Sajjadi
*Assistant Examiner* — Anna Falkowitz
(74) *Attorney, Agent, or Firm* — Sughrue Mion, PLLC

(57) ABSTRACT

A solubilizing composition containing (A) at least one oily component selected from esters of oleic acid with alcohols having 1 to 3 carbon atoms and triglycerides of fatty acids having 6 to 12 carbon atoms, (B) a polyoxyethylenesorbitan fatty acid ester, (C) a polyhydric alcohol which is liquid between 15° C. and 25° C., and (D) one or more acidic phospholipids where the fatty acid constituting an acyl group thereof is selected from saturated fatty acids having 6 to 14 carbon atoms and unsaturated fatty acids having 16 to 18 carbon atoms, which contains 20 to 40% by weight of the component (A), 30 to 45% by weight of the component (B), 15 to 40% by weight of the component (C), and 0.5 to 4% by weight of the component (D), based on 100% by weight of a total amount of the components (A) to (D).

18 Claims, 1 Drawing Sheet

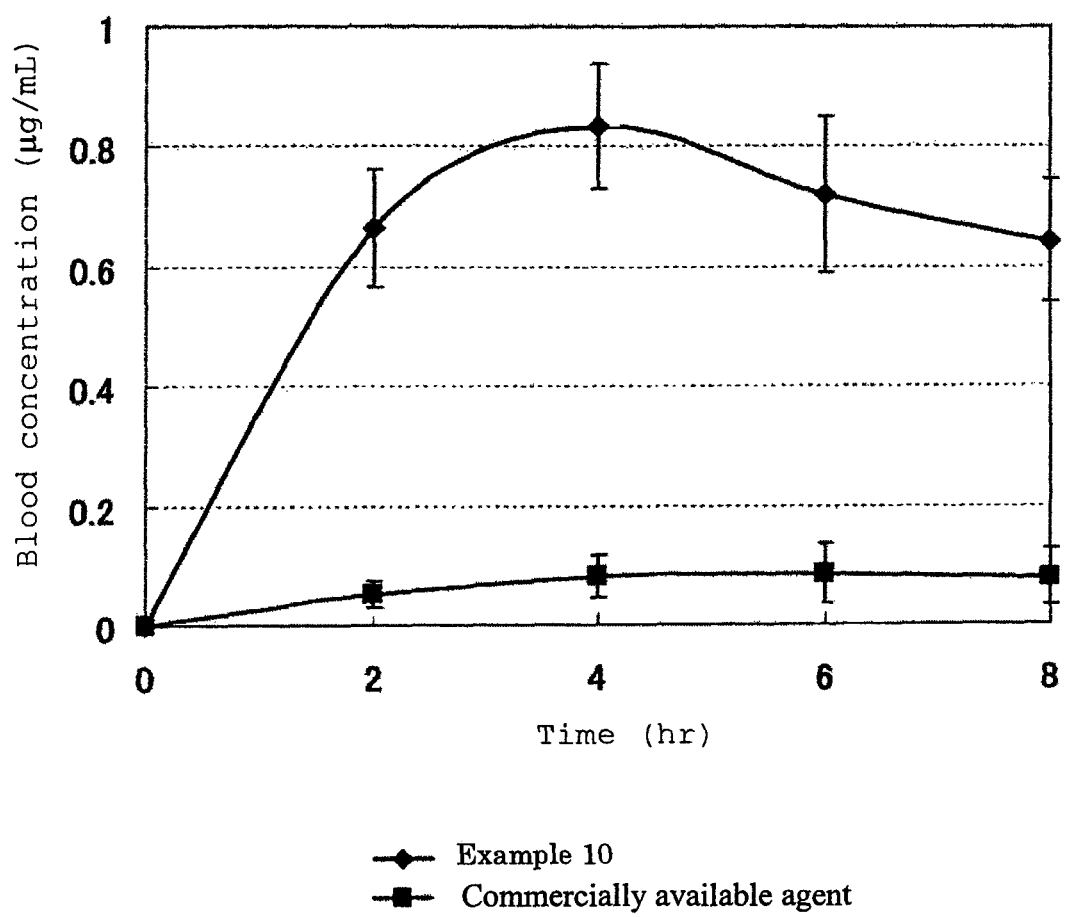

SOLUBILIZING COMPOSITION

BACKGROUND OF THE INVENTION

1. Field of the Invention

The present invention relates to a composition for solubilizing a hardly water-soluble medical agent, as well as a pre-concentrate for solubilizing a hardly water-soluble compound, which contains the composition and the compound.

2. Description of the Related Art

A hardly water-soluble medical agent has a problem that intestinal absorbability and bioavailability are low owing to its low solubility in water. Moreover, also in the development of new drugs, there frequently arises an extremely serious problem in the case where the drugs are hardly water-soluble. Particularly, since most of new-drug candidate substances for antimalignant tumor drugs, immunosuppressive agents, antibiotics, antifungal agents, antihyperlipidemic agents, antiinflammatory agents, and the like are hardly water-soluble and cannot be solubilized, various tests such as toxicity tests cannot be performed and thus the substances frequently become pending or drop out during their development even when they have a sufficient pharmacological activity.

Thus, hitherto, as formulation of a hardly water-soluble medical agent, there has been investigated solubilization using a thermodynamically stable microemulsion.

However, for microemulsification, a high-pressure emulsifier is frequently used in order to reduce particle size and there is a problem that activity may decrease depending on a medical agent under the influence of friction heat at high-pressure emulsification. Moreover, even when oil drops themselves in the microemulsion are stable (small particle size), by the crystal growth of the hardly water-soluble medical agent during storage, the medical agent may be frequently precipitated. In addition, since most of the composition in microemulsion is water, the microemulsion cannot be encapsulated (gelatin to be used as a capsule film is dissolved), so that the drug form is basically limited to a liquid. Therefore, there are problems in view of compliance, for example, bitter taste originated from the medical agent and increased dosage per one dose.

For example, in WO03/066025A1, transparent aqueous gel and aqueous solution of β-carotene have been prepared using a polyol, an ester of an unsaturated fatty acid, a surfactant, and water. As a specific example, an aqueous gel containing β-carotene has been prepared using ethyl linoleate, polysorbate 80, glycerin, lecithin, water, and the like. The composition is different from the pre-concentrate in the invention in the facts that ethyl linoleate is substantially used as an unsaturated fatty acid ester and lecithin (main ingredient: phosphatidylcholine) is used as an additional component in addition to the fact that water is contained.

Since the composition is a preparation containing water in a high ratio, a gelatin capsule cannot be applied and, particularly in the case of an aqueous solution, there is a problem of stability as a preparation, e.g., increase in particle size with the passage of time through occurrence of aggregation and integration of particles. Moreover, a highly crystalline hardly water-soluble medical agent cannot be dissolved in the composition in a high concentration. Furthermore, the composition is a formulation or a preparation method limited to β-carotene and, since heating at 160 to 180° C. is necessary at the stage of its preparation, activity of a common hardly water-soluble medical agent considerably decreases.

Moreover, in WO97/36611A1, an oil-in-water type emulsion of cyclosporin is prepared using a middle-chain fatty acid triglyceride, a phospholipid, and water (further using a free fatty acid, glycerin, and a surfactant as additional components). As a specific example, an oil-in-water type emulsion of cyclosporin A is prepared using a middle-chain fatty acid triglyceride (trade name: miglyol 810), linoleic acid, TWEEN 20, glycerin, an egg phospholipid, dimyristoylphosphatidylglycerol (DMPG), and water. The composition is different from the pre-concentrate in the invention in the facts that linoleic acid which is a free fatty acid is used as an additional component and the egg phospholipid (main ingredient: phosphatidylcholine) is contained as a phospholipid component in addition to the fact that water is contained.

Furthermore, in U.S. Pat. No. 5,658,898, a nanoemulsion of staurosporin derivative is prepared using a triglyceride, a phospholipid, a partial fatty acid ester of polyoxyethylene sorbitan, and water. As a specific example, a nanoemulsion is prepared using a middle-chain fatty acid triglyceride (trade name: miglyol 812), polysorbate 80, lecithin derived from soybean oil (trade name: LIPOID S 100), and water. The composition is different from the pre-concentrate in the invention in the facts that a polyhydric alcohol is not contained and lecithin derived from soybean oil (main ingredient: phosphatidylcholine) is used as a phospholipid in addition to the fact that water is contained.

With regard to the compositions described in WO03/066025A1, WO97/36611A1, and U.S. Pat. No. 5,658,898, emulsification by a high-pressure emulsifier is required for preparing an objective emulsion, and the compositions are deactivated under the influence of high-pressure emulsification depending on a medical agent. Moreover, since the ratio of an aqueous phase is high, direct gelatin encapsulation is impossible. However, a pre-concentrate with a component other than water does not have self-emulsifying ability (self-micro- or nano-emulsifying ability) and its drug form for oral administration is limited to a liquid. In the case where the drug form of the hardly water-soluble medical agent is a liquid (emulsion), aggregation and integration of particles occur and particle size increases with the passage of time, so that stability as a preparation cannot be said to be sufficient.

Based on these backgrounds, recently, as a preparation of a hardly water-soluble medical agent, there has been developed a self-emulsification (self-microemulsification) type drug delivery system (SMEDDS; also called as microemulsion pre-concentrate (MEPC)) wherein the preparation itself does not contain water and is easily dispersed or dissolved in water. However, there has been hitherto not known a solubilizing composition which satisfies all requirements, demanded as performance of the SMEDDS preparation, that it is stable as a pre-concentrate, a medical agent can be contained in a high concentration, self-emulsification (self-microemulsification) is possible, a dispersion rate into water is high, particle size after solubilization is small, and intestinal absorbability is high and which is applicable to various hardly water-soluble medical agents.

3. Problems to be Solved by the Invention

An object of the invention is to provide a solubilizing composition which satisfies all requirements demanded for the aforementioned SMEDDS preparation and also is widely applicable to various hardly water-soluble medical agents, to prepare a solubilizing pre-concentrate of a hardly water-soluble medical agent using the composition, and, as a result, to improve bioavailability of the hardly water-soluble medical agent.

SUMMARY OF THE INVENTION

The invention is based on the finding that a solubilizing pre-concentrate containing substantially no water and satisfying all requirement that a medical agent can be contained in a high concentration, self-emulsification (self-microemulsification) is possible, a dispersion rate into water is high, and particle size after dispersion is small can be prepared, regardless of the kind of a hardly water-soluble compound, by containing (A) at least one oily component selected from esters of oleic acid with alcohols having 1 to 3 carbon atoms and triglycerides of fatty acids having 6 to 12 carbon atoms, (B) a polyoxyethylenesorbitan fatty acid ester, (C) a polyhydric alcohol which is liquid between 15° C. and 25° C., and (D) one or more acidic phospholipids where the fatty acid constituting the acyl group is selected from saturated fatty acids having 6 to 14 carbon atoms and unsaturated fatty acids having 16 to 18 carbon atoms in an appropriate mixing ratio.

Namely, the invention is as follows.

(1) A solubilizing composition comprising (A) at least one oily component selected from esters of oleic acid with alcohols having 1 to 3 carbon atoms and triglycerides of fatty acids having 6 to 12 carbon atoms, (B) a polyoxyethylenesorbitan fatty acid ester, (C) a polyhydric alcohol which is liquid between 15° C. and 25° C., and (D) one or more acidic phospholipids where the fatty acid constituting an acyl group thereof is selected from saturated fatty acids having 6 to 14 carbon atoms and unsaturated fatty acids having 16 to 18 carbon atoms.

(2) The solubilizing composition according to the above (1), which contains 20 to 40% by weight of the component (A), 30 to 45% by weight of the component (B), 15 to 40% by weight of the component (C), and 0.5 to 4% by weight of the component (D), based on 100% by weight of the total amount of the components (A) to (D).

(3) The solubilizing composition according to the above (1) or (2), which further contains (E) ethanol in an amount of 0.1 to 10% by weight based on the total amount of the components (A) to (D).

(4) The solubilizing composition according to any one of the above (1) to (3), wherein the component (A) is selected from ethyl oleate and triglycerides of fatty acids having 8 to 10 carbon atoms.

(5) The solubilizing composition according to any one of the above (1) to (4), wherein the polyoxyethylenesorbitan fatty acid ester (B) is an ester of a fatty acid having 12 to 18 carbon atoms and the average addition mole number of the oxyethylene group is 15 to 25.

(6) The solubilizing composition according to the above (5), wherein the polyoxyethylenesorbitan fatty acid ester (B) is an ester of a fatty acid having 12 or 18 carbon atoms.

(7) The solubilizing composition according to any one of the above (1) to (6), wherein the polyhydric alcohol (C) is propylene glycol or glycerin.

(8) The solubilizing composition according to any one of the above (1) to (7), wherein the acidic phospholipid (D) is selected from phosphatidylglycerol, phosphatidylserine, and phosphatidic acid.

(9) The solubilizing composition according to the above (8), wherein the fatty acid constituting the acyl group of the acidic phospholipid (D) is selected from saturated fatty acids having 6 to 14 carbon atoms and oleic acid.

(10) A solubilizing pre-concentrate of a hardly water-soluble compound, which comprises the solubilizing composition according to any one of the above (1) to (9) and the compound.

(11) The pre-concentrate according to the above (10), which is a pharmaceutical composition containing the hardly water-soluble compound as an active component.

The solubilizing pre-concentrate of the invention is a stable transparent solution having no factors for destabilization as a preparation, such as precipitation of a medical agent and aggregation and integration of particles, and also is a pre-concentrate capable of gelatin capsulation. Moreover, since the pre-concentrate has a novel composition that the above components (A) to (D) are contained and, preferably they are contained in the mixing ratio as described above, the pre-concentration satisfies all the requirements that a medical agent can be contained in a high concentration, self-emulsification (self-microemulsification) is possible, a dispersion rate into water is high, and particle size after dispersion is small and is applicable to various hardly water-soluble medical agents. Furthermore, the solubilizing pre-concentrate of the invention also has one characteristic that intestinal absorbability at oral administration is high.

BRIEF DESCRIPTION OF THE DRAWINGS

FIG. 1 is a drawing illustrating change in blood concentration with regard to Example 10 and a commercially available preparation.

DETAILED DESCRIPTION OF THE INVENTION

The following will explain the present invention further in detail.

The invention provides a pre-concentrate for solubilizing a hardly water-soluble compound, i.e., a "solubilizing pre-concentrate (hereinafter sometimes referred to as a "pre-concentrate of the invention") as well as a composition containing substantially no water which can prepare, when blended with the hardly water-soluble compound, the solubilizing pre-concentrate satisfying individual requirements that a hardly water-soluble compound can be contained in a high concentration, self-emulsification (self-microemulsification) is possible, a dispersion rate into water is high, and particle size after dispersion is small, i.e., a "solubilizing composition (hereinafter sometimes referred to as a "composition of the invention"). In this connection, "solubilization" means that the hardly water-soluble compound is dissolved or dispersed in water in a living body in such a degree that a sufficient living-body absorbability for exhibiting desired physiological activity of the hardly water-soluble medical agent in the pre-concentrate is obtained. Therefore, the term is used with the meaning including microemulsification.

In order to exhibit the above properties and the previous effects, the composition of the invention has an intrinsic nature that it contains substantially no water. The term "to contain substantially no water" means that it contains water in such a degree that, when a hardly water-soluble compound is added to form the pre-concentrate of the invention, precipitation of the compound through crystal growth does not occur during storage and conventional capsule film such as gelatin is not dissolved. Specifically, the amount of water in the composition of the invention is preferably 0.5% by weight or less, more preferably 0.3% by weight or less based on the total weight of the composition of the invention.

In the invention, the "hardly water-soluble compound" refers to a compound whose solubility in water at 20° C. is 10 mg/mL or less. The composition of the invention is applicable to a compound having a solubility in water at 20° C. of preferably 1 mg/mL or less, more preferably 0.1 mg/mL or less. Specifically, as the hardly water-soluble compound, there may be, for example, mentioned compounds usable as medicines and/or veterinary medicines, e.g., indole derivatives such as indomethacin, acemetacin, sulindac, proglumetacin maleate, and pindolol; salicylic acid derivatives such as aspirin and diflunisal; phenylpropionic acid derivatives such as ibuprofen, ketoprofen, naproxen, and pranoprofen; anthranilic acid derivatives such as mefenamic acid and flufenamic acid aluminum; benzothiazine derivatives such as piroxicam and ampiroxicam; thiopheneacetic acid derivatives such as tiaprofenic acid; steroid derivatives such as medroxyprogesterone acetate, chlormadinone acetate, danazol, fluorometholone, dexamethasone, hydrocortisone, prednisolone, methylprednisolone, and betamethasone; folic acid derivatives such as folic acid and methotrexate; taxane derivatives such as paclitaxel and docetaxel hydrate; purine derivatives such as mercaptopurine; pyrimidine derivatives such as fluorouracil and tegafur; peptide-based agents such as cyclosporine A; pyridonecarboxylic acid derivatives (newquinolone antimicrobials) such as enoxacin, norfloxacin, ofloxacin, levofloxacin, ciprofloxacin hydrochloride, tosufloxacin tosilate, sparfloxacin, lomefloxacin hydrochloride, and fleroxacin; triazole derivatives such as itraconazole and fluconazole; fibrate-based agents such as clofibrate, clinofibrate, and bezafibrate; dihydropyridine derivatives such as nifedipine; benzodiazepine derivatives such as triazolam, diazepam, nitrazepam, flurazepam hydrochloride, midazolam, and estazolam; butyrophenone derivatives such as haloperidol and droperidol; xanthine derivatives such as theophylline; digitalis derivatives such as digitoxin and digoxin; barbituric acid derivatives such as phenobarbital; hydantoin derivatives such as phenytoin; imidazole derivatives such as cimetidine; benzimidazole derivatives such as omeprazole and lansoprazole; thiazole derivatives such as famotidine; statin-based agents such as simvastatin; as well as probucol, mitomycin C, tamoxifen citrate, cisplatin, tacrolimus hydrate, griseofulvin, aciclovir, dipyridamole, prazosin hydrochloride, reserpine, verapamil hydrochloride, atenolol, sulpiride, clemastine fumarate, terfenadine, cyproheptadine hydrochloride, oxethazaine, sucralfate, gefarnate, rebamipide, metoclopramide, retinol palmitate, riboflavin butyrate, pyridoxal phosphate, mecobalamin, tocopherol acetate, phytonadione, menatetrenone, furosemide, indapamide, spironolactone, tranilast, bromhexine hydrochloride, benzbromarone, allopurinol, tolbutamide, levodopa, and the like but the compound is not particularly limited thereto so far as it has the above solubility. For example, it also includes food additives in general foods such as processed foods and beverages, ingredients for health-promoting foods such as specified health foods and nutritional functional foods and supplements, or pesticide compounds, and the like.

The concentration of the hardly water-soluble compound in the pre-concentrate of the invention is preferably 0.1 to 20% by weight, more preferably 0.2 to 15% by weight, further preferably 0.5 to 10% by weight.

The component (A) in the invention is at least one oily component selected from esters of oleic acid with alcohols having 1 to 3 carbon atoms and triglycerides of fatty acids having 6 to 12 carbon atoms. As specific compounds of the esters of oleic acid with alcohols having 1 to 3 carbon atoms, methyl oleate, ethyl oleate, and propyl oleate may be mentioned, and as particularly preferred one, ethyl oleate may be mentioned.

The acyl groups of the triglycerides in the triglycerides of fatty acids having 6 to 12 carbon atoms may be one kind or two kinds or more. Preferably, there may be mentioned triglycerides of fatty acids having 8 to 10 carbon atoms. As commercially available products, there may be mentioned NOFABLE EO-99, NOFABLE EO-85S (ethyl oleate, manufactured by NOF Corporation), Panasate 810 (triglycerides of fatty acids having 6 to 12 carbon atoms), and the like.

The component (B) in the invention is a polyoxyethylenesorbitan fatty acid ester, preferably an ester of a fatty acid having 12 to 18 carbon atoms and a polyoxyethylenesorbitan fatty acid ester wherein an average addition moles of the oxyethylene group is 15 to 25, more preferably an ester of a fatty acid having 12 to 18 carbon atoms and a polyoxyethylenesorbitan fatty acid ester wherein an average addition moles of the oxyethylene group is 15 to 25. As specific compounds, there may be, for example, mentioned polyoxyethylene(20)sorbitan monolaurate (polysorbate 20), polyoxyethylene(20)sorbitan monopalmitate (polysorbate 40), polyoxyethylene(20)sorbitan monostearate (polysorbate 60), polyoxyethylene(20)sorbitan monooleate (polysorbate 80), and the like. Preferably, there may be mentioned polyoxyethylene(20)sorbitan monolaurate (polysorbate 20), polyoxyethylene(20)sorbitan monooleate (polysorbate 80), and the like, and more preferably, polyoxyethylene(20)sorbitan monooleate (polysorbate 80) may be mentioned. As commercially available products, Polysorbate 20 (HX) (polysorbate 20), Polysorbate 80 (HX) (polysorbate 80) (both are manufactured by NOF Corporation), and the like may be mentioned.

The component (C) in the invention is not particularly limited so far as it is a polyhydric alcohol which is liquid between 15° C. and 25° C. but there may be preferably mentioned propylene glycol, glycerin, polyethylene glycol 200, polyethylene glycol 300, polyethylene glycol 400, and polyethylene glycol 600, and more preferably, propylene glycol or glycerin may be mentioned. Most preferably, there may be mentioned a combination of glycerin and propylene glycol wherein the ratio of glycerin/propylene glycol is 1 to 1.5. Since the use of these compounds as the component (c) remarkably increases the dispersion rate of the solubilizing pre-concentrate into water, they are very useful for oral preparations.

The component (D) in the invention is one or more acidic phospholipids where the fatty acid constituting the acyl group is selected from saturated fatty acids having 6 to 14 carbon atoms and unsaturated fatty acids having 16 to 18 carbon atoms. In the invention, the "acidic phospholipid" means a phospholipid which is anionic as a whole molecular structure, wherein the hydrophilic portion of the phospholipid is phosphatidylglycerol, phosphatidic acid, phosphatidylserine, or the like. Preferably, the acidic phospholipid is phosphatidylglycerol, phosphatidylserine, or phosphatidic acid. More preferred is phosphatidylglycerol, phosphatidylserine, and phosphatidic acid wherein the fatty acid constituting the acyl group of the acidic phospholipid is selected from saturated fatty acids having 6 to 14 carbon atoms and oleic acid.

The acyl group in one molecule of the acidic phospholipid comprises at least one molecule of a fatty acid selected from saturated fatty acids having 6 to 14 carbon atoms and unsaturated fatty acids having 16 to 18 carbon atoms, and a lysoform is also included.

As commercially available products, there may be mentioned COATSOME MG-4040LS (dimyristoylphosphatidylglycerol), COATSOME MS-8181LS (dioleoylphosphatidylserine), COATSOME MA-4040LS (dimyristoylphosphatidic acid) (all manufactured by NOF Corporation), and the like.

The mixing ratio of the components (A) to (D) in the composition of the invention is not particularly limited so far as a solubilizing pre-concentrate can be prepared, the pre-concentrate satisfying individual requirements that a hardly water-soluble compound can be contained in a high concentration when blended with the hardly water-soluble compound, self-emulsification (self-microemulsification) is possible, a dispersion rate into water is high, and particle size after dispersion is small. However, they are contained in a mixing ratio of preferably 20 to 40% by weight of (A), 30 to 45% by weight of (B), 15 to 40% by weight of (C), and 0.5 to 4% by weight of (D), more preferably 20 to 38% by weight of (A), 32 to 45% by weight of (B), 15 to 38% by weight of (C), and 0.5 to 3% by weight of (D), further preferably 20 to 35% by weight of (A), 34 to 45% by weight of (B), 15 to 35% by weight of (C), and 0.5 to 2% by weight of (D), based on 100% by weight of the total amount of the components (A) to (D).

With regard to the compositional ratio of the solubilizing composition of the invention, in the case where the component (A) is lower than 20% by weight based on the total weight of the components (A) to (D), the dissolved amount of the hardly water-soluble medical agent in the solubilizing composition is small and as a result, in order to take an appropriate amount of the agent, it is required to increase the size of one capsule or increase the number of capsules to be taken at a time, so that there is a problem in view of compliance. In addition, when the ratio of the oily component is small, a high intestinal absorbability cannot be expected. Contrarily, when the component (A) is contained in an amount of higher than 40% by weight based on the total weight of the components (A) to (D), the ratio of the component (B) (surfactant) relatively decreases, so that there are problems of phase-separation of the pre-concentrate and increase in particle size after dispersion in water. In the case where the ratio of the component (B) is lower than 30% by weight based on the total weight of the components (A) to (D), there are problems for the same reasons. In the case where the ratio of the component (B) is higher than 45% by weight based on the total weight of the components (A) to (D), the ratio of the component (B) relative to the total weight of the pre-concentrate increases, so that the pre-concentrate may be gelled when dispersed in water, the dispersion time may be remarkably prolonged, and the dispersion time may vary widely. Moreover, in the case where the ratio of the component (C) is lower than 15% by weight based the total weight of the components (A) to (D), the dispersion time may be prolonged and the dispersion time may vary widely. Contrarily, in the case where the ratio of the component (C) is larger than 40% by weight based on the total weight of the components (A) to (D), the ratio of the component (A) and/or (B) becomes relatively small, so that there arise the same problems as above. The component (D) is important for dissolving the pre-concentrate itself homogeneously and, in the case where the ratio thereof is lower than 0.5% by weight based on the total weight of the components (A) to (D), the effect is not observed and hence the pre-concentrate is phase-separated. In the case where the ratio thereof is higher than 4% by weight based on the total weight of the components (A) to (D), there are problems of precipitation of the component (D) in the pre-concentrate and increase in particle size at dispersion into water or of precipitation of the component (D) and delay of dispersion rate into water owing to increase in viscosity. In order to further enhance stability, the ratio of (C)/(D) (weight ratio) is preferably 13 to 80, more preferably 16 to 70.

Moreover, provided that the above weight ratio is satisfied, the composition of the invention may contain the other component(s) within the range where the effect of the invention is inhibited. For example, (E) ethanol may be contained in the mixing ratio of (E) 0.1 to 10% by weight, the total amount of the components (A) to (D) being regarded as 100% by weight. When the component (E) is used, the solubility of the hardly water-soluble compound in the composition of the invention can be remarkably increased. However, when the ratio becomes more than 10% by weight based on the total weight of the components (A) to (D), there arise problems such that the particle size after dispersion into water increases and an adverse effect of ethanol may possibly exhibited after intestinal absorption.

As components other than the component (E), there may be mentioned various additives suitable for the uses of the objective hardly water-soluble compound, for example, pharmaceutically acceptable carriers, excipients, and the like in the case where the hardly water-soluble compound is a pharmaceutical compound.

Moreover, as a method for preparing a solubilizing pre-concentrate according to the invention, for example, there may be mentioned a method of directly dissolving a hardly water-soluble compound into the composition of the invention but the method is not limited thereto and the following method may be, for example, mentioned in addition thereto.

Into (i) the solubilizing composition is added (ii) a solution of the hardly water-soluble compound dissolved in an organic solvent in a ratio of (i):(ii)=2:1 to 1:10 (v/v), the whole was thoroughly mixed to form a homogeneous solution, and then the organic solvent is removed by a method such as evaporation. As the organic solvent, a volatile organic solvent such as methanol, ethanol, isopropanol, acetonitrile, acetone, chloroform, or dichloromethane is preferred. Moreover, the temperature and time for evaporation may be set depending on the physical properties of the medical agent.

In the case where the pre-concentrate of the invention obtained as above is a pharmaceutical composition, it can be further formulated into a drug form suitable for oral or parenteral administration. As the composition for oral administration, there may be mentioned solid or liquid drug forms, specifically tablets (inclusive of sugar-coated tablets and film-coated tablets), pills, granules, powders, capsules (inclusive of soft capsules), syrups, emulsions, suspensions, and the like. Such a composition is produced by a known method and may contain a carrier, a diluent, or an excipient commonly used in a formulation field. In the case of administration as a syrup, an emulsion, a suspension, or the like, it is desirable to prepare it just before use. In the sense of using the characteristic of the pre-concentrate of the invention that water is substantially not contained, it is preferred to use the pre-concentrate by filling it into a capsule of gelatin or the like. As the composition for parenteral administration, for example, injections, suppositories, and the like are used and the injections may include drug forms such as intravenous injections, subcutaneous injections, percutaneous injections, intramuscular injections, and drip injections. Such injections can be prepared according to known methods. As a method for preparing injections, they can be, for example, prepared by dissolving, suspending, or emulsifying the pre-concentrate of the invention in an aseptic aqueous liquid or oily liquid commonly used for injections according to needs. As the aqueous liquid for injections, for example, physiological saline, isotonic liquids containing glucose or the other auxiliary agent is used and may be used in combination with an appropriate solubilizing auxiliary such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], or the like. As the oily liquid, sesame oil, soybean oil, or the like is used, and benzyl benzoate, benzyl alcohol, or the like may be used in combination as a solubilizing auxiliary. In the case where an injection is formed by dissolution, suspension, or emulsification into an aqueous liquid or an oily liquid, it is desirable to conduct the operation of dissolution, suspension, or emulsification just before use. Moreover, the suppositories for use in rectal administration can be also prepared by mixing the pre-condensate of the invention into a usual base for suppositories.

The solubility in water of the hardly water-soluble compound in the pre-concentrate of the invention considerably varies depending on the kind of the compound but the final concentration after dispersion into water (microemulsification) is 5 to 10,000 times, preferably 10 to 5,000 times, more preferably 20 to 2,000 times the solubility in water of each hardly water-soluble compound itself.

Moreover, in the invention, the particle size after dispersion of the solubilizing pre-concentrate into water is preferably 200 nm or less, more preferably 100 nm or less.

EXAMPLES

The following will illustrate the invention in greater detail with reference to Examples and Comparative Examples, but the invention should not be construed as being limited to the following Examples.

Table 1 shows product names and common names of the compounds used in the production of solubilizing compositions described in Examples and Comparative Examples.

TABLE 1

| Substance name | Product name *1) |
| --- | --- |
| Ethyl oleate | NOFABLE EO-99 |
| Middle-chain fatty acid triglyceride (fatty acid having 6 to 12 carbon atoms) | Panasate 810 |
| Polyoxyethylene(20)sorbitan monooleate (polysorbate 80) | Polysorbate 80 (HX) |

TABLE 1-continued

| Substance name | Product name *1) |
| --- | --- |
| Polyoxyethylene(20)sorbitan monolaurate (polysorbate 20) | Polysorbate 20 (HX) |
| Glycerin | Concentrated glycerin-S |
| Dimyristoylphosphatidylglycerol (DMPG) | COATSOME MG-4040LS |
| Dimyristoylphosphatidic acid (DMPA) | COATSOME MA-4040LS |
| Hydrogenated soybean-derived phospholipid | COATSOME NC-21 |
| Hydrogenated soybean-derived phospholipid | COATSOME NC-61 |
| Non-hydrogenated soybean-derived phospholipid | COATSOME NC-20 |
| Non-hydrogenated egg yolk-derived phospholipid | COATSOME NC-50 |
| Distearoylphosphatidylcholine (DSPC) | COATSOME MC-8080 |
| Monostearoylphosphatidylcholine (MSPC) | COATSOME MC-80H |
| Dimyristoylphosphatidylcholine (DMPC) | COATSOME MC-4040 |
| Dipalmitoylphosphatidylglycerol (DPPG) | COATSOME MG-6060LS |
| Dipalmitoylphosphatidic acid (DPPA) | COATSOME MA-6060LS |

*1) The sales company of the above all products is NOF Corporation.

In the following, with regard to Examples, Table 2 shows compositional ratios of solubilizing compositions. In this connection, the numerals in the Table are weight ratios (% by weight) to the total amount of the components (A) to (D).

Examples 1 to 9

TABLE 2

| | | Example 1 | Example 2 | Example 3 | Example 4 | Example 5 | Example 6 | Example 7 | Example 8 | Example 9 |
| --- | --- | --- | --- | --- | --- | --- | --- | --- | --- | --- |
| (A) | Ethyl oleate | 29.0 | 30.2 | 30.2 | 20.0 | 20.0 | — | 31.0 | 31.0 | 31.0 |
| | Middle-chain fatty acid triglyceride (6 to 12 carbon atoms) | — | — | — | — | — | 20.0 | — | — | — |
| (B) | Polysorbate 80 | 35.0 | 35.3 | 35.3 | 45.0 | — | 45.0 | 34.9 | 34.9 | 34.9 |
| | Polysorbate 20 | — | — | — | — | 45.0 | — | — | — | — |
| (C) | Propylene glycol | 15.0 | 15.7 | 15.7 | 15.0 | 15.0 | 15.0 | 15.5 | 15.5 | 15.5 |
| | Glycerin | 19.0 | 17.6 | 17.6 | 18.8 | 19.5 | 18.8 | 17.4 | 17.4 | 17.4 |
| (D) | DMPG | 2.0 | 1.2 | — | 1.2 | 0.5 | 1.2 | 1.2 | 1.2 | 1.2 |
| | DMPA | — | — | 1.2 | — | — | — | — | — | — |
| (E) | Ethanol | — | — | — | — | — | — | 1.9 | 3.9 | 7.8 |

The solubilizing composition of Example 1 was produced by stirring the components (A) to (D) at about 80° C. to effect complete dissolution. The solubilizing compositions of Examples 2 to 6 were also produced in the same manner. The solubilizing composition of Example 7 was produced by stirring the components (A) to (D) at about 80° C. to effect complete dissolution and subsequently adding the component (E) at ordinary temperature, followed by sufficient mixing and homogeneous dissolution. The solubilizing compositions of Examples 8 and 9 were also produced in the same manner.

In the following, with regard to Comparative Examples, Tables 3 and 4 show compositional ratios of the solubilizing compositions. In this connection, the numerals in the Tables are weight ratios (% by weight) in the solubilizing compositions. Moreover, the compounds for comparison with the components (A) to (D) are shown as a component (A)' (oily component) and a component (D)' (phospholipid component).

Comparative Examples 1 to 8

TABLE 3

|   |   | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| (A) | Ethyl oleate | 11.9 | — | 8.8 | — | — | 31 | 20 | — |
|  | Middle-chain fatty acid triglyceride (6 to 12 carbon atoms) | — | 17.7 | — | 33.3 | 62 | — | — | 20 |
| (A)' | Linoleic acid | — | — | — | — | 20.7 | — | — | — |
| (B) | Polysorbate 80 | 50.6 | 29.4 | 52.9 | 50 | — | 35 | 45 | 45 |
|  | Polysorbate 20 | — | — | — | — | 2.1 | — | — | — |
| (C) | Propylene glycol | 35.7 | 23.6 | — | — | — | 15 | 15 | 15 |
|  | Glycerin | — | — | 35.3 | — | 10.3 | 19 | 20 | 20 |
| (D) | DMPG | — | — | — | — | 0.83 | — | — | — |
| (D)' | Hydrogenated soybean-derived phospholipid | 1.8 | — | 3 | — | — | — | — | — |
|  | Non-hydrogenated soybean-derived phospholipid | — | — | — | 16.7 | — | — | — | — |
|  | Non-hydrogenated egg yolk-derived phospholipid | — | — | — | — | 4.1 | — | — | — |
|  | DSPC | — | 9.8 | — | — | — | — | — | — |
|  | MSPC | — | 19.6 | — | — | — | — | — | — |

Comparative Examples 9 to 15

TABLE 4

|   |   | Comparative Example 9 | Comparative Example 10 | Comparative Example 11 | Comparative Example 12 | Comparative Example 13 | Comparative Example 14 | Comparative Example 15 |
|---|---|---|---|---|---|---|---|---|
| (A) | Ethyl oleate | 29 | 29 | 30.2 | 30.2 | 30.4 | 29.1 | — |
| (A)' | Soybean oil | — | — | — | — | — | — | 30.2 |
| (B) | Polysorbate 80 | 35 | 35 | 35.3 | 35.3 | 35 | 34 | 35.3 |
| (C) | Propylene glycol | 15 | 15 | 15.7 | 15.7 | 15 | 15.1 | 15.7 |
|  | Glycerin | 19 | 19 | 17.6 | 17.6 | 19 | 17 | 17.6 |
| (D) | DMPG | — | — | — | — | 0.4 | 4.9 | 1.2 |
| (D)' | Hydrogenated soybean-derived phospholipid | 2 | — | — | — | — | — | — |
|  | DMPC | — | 2 | — | — | — | — | — |
|  | DPPG | — | — | 1.2 | — | — | — | — |
|  | DPPA | — | — | — | 1.2 | — | — | — |

The solubilizing composition of Comparative Example 1 was produced by gradually adding the components (A) and (C) to the component (B) heated at about 120° C. and further adding the component (D)', followed by thorough mixing. The solubilizing composition of Comparative Example 2 was produced by adding the components (A), (B), and (D)' to the component (C) and heating the whole at about 50° C. for about 12 hours. The solubilizing composition of Comparative Example 3 was produced by adding the components (A) and (C) to the component (B) heated to about 130° C., continuing stirring at 85 to 90° C. until the mixture was dissolved, and, after dissolution, adding the component (D)', followed by thorough mixing. The solubilizing composition of Comparative Example 4 was produced by mixing the component (A) and the component (B) and subsequently adding the component (D)', followed by stirring at about 80° C. until homogeneous dissolution. The solubilizing composition of Comparative Example 5 was produced by mixing the components (A) and (A)', adding the components (D) and (D)' to the mixture at about 60 to 70° C., and adding the component (B) and the component (C), followed by thorough mixing. The solubilizing composition of Comparative Example 6 was produced by thoroughly mixing individual components at about 80° C. The solubilizing compositions of Comparative Examples 7 to 15 were also produced in the same manner.

With regard to the solubilizing compositions of Examples 1 to 9, Table 5 shows results of evaluating performance in view of appearance of the solubilizing compositions, dispersion rate of the solubilizing compositions in water, and particle size of microemulsions after dispersion.

<Evaluation Method>

Appearance of Solubilizing Composition

The appearance of the solubilizing compositions at ordinary temperature after dissolution of individual components was evaluated. Furthermore, the appearance of the solubilizing compositions after standing for one day was evaluated.

○: a homogeneous transparent liquid

Δ: a semi-transparent, slightly turbid liquid x: a heterogeneous state such as phase separation and precipitation or a fluidity-less state such as solidification Dispersion Rate While 10 mL of water (vessel: a 20 mL screw tube) was stirred at 400 rpm using a magnetic stirrer, 100 μL of a solubilizing composition was added thereto and time required for homogeneous dispersion from the addition was measured.
S: within 1 minute, A: 1 to 3 minutes, B: 3 to 5 minutes, C: 5 to 10 minutes, D: 10 to 20 minutes, E: 20 minutes or more Particle Size With regard to the microemulsions after measurement of dispersion rate, particle sizes were measured using a dynamic light scattering-type particle size-measuring machine.

TABLE 5

| Appearance of pre-concentrate | Example 1 | Example 2 | Example 3 | Example 4 | Example 5 | Example 6 | Example 7 | Example 8 | Example 9 |
|---|---|---|---|---|---|---|---|---|---|
| After preparation | ○ | ○ | ○ | ○ | ○ | ○ | ○ | ○ | ○ |
| After 1 day | ○ | ○ | ○ | ○ | ○ | ○ | ○ | ○ | ○ |
| Dispersion rate | S | A | A | A | S | S | A | S | S |
| Particle diameter (nm) | 13.3 | 9.0 | 26.6 | transparent *2) | 21.6 | 17.4 | 28.6 | 49.7 | 62.9 |

*2) about 10 nm or less (estimated)

With regard to the solubilizing compositions of Comparative Examples 1 to 15, evaluation of performance was conducted as in Examples 1 to 9. Results are shown in Tables 6 and 7. In this connection, the solubilizing compositions whose appearance evaluation after 1 day was x was judged to be improper as preparations because of heterogeneous composition and hence the measurement of dispersion rate and particle size was not carried out but, with regard to Comparative Example 2, the dispersion rate and particle size just after dissolution of the solubilizing composition by heating at about 80° C. were measured to evaluate the composition.

TABLE 6

| Appearance of pre-concentrate | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| After preparation | Δ | x | x | ○ | x | ○ | Δ | ○ |
| After 1 day | Δ | x | x | ○ | x | x | x | x |
| Dispersion rate | A | E | — | E | — | — | — | — |
| Particle diameter (nm) | 24574 | 31502 | — | 61.7 | — | — | — | — |

TABLE 7

| Appearance of pre-concentrate | Comparative Example 9 | Comparative Example 10 | Comparative Example 11 | Comparative Example 12 | Comparative Example 13 | Comparative Example 14 | Comparative Example 15 |
|---|---|---|---|---|---|---|---|
| After preparation | x | ○ | Δ | x | ○ | ○ | x |
| After 1 day | x | x | x | x | x | x | x |
| Dispersion rate | — | — | — | — | — | — | — |
| Particle diameter (nm) | — | — | — | — | — | — | — |

Moreover, the following will show examples to which various hardly water-soluble medical agents are applied using the solubilizing composition of Example 2.

Example 10

After 0.93 g of probucol (PRB) was added to 10.63 g of the solubilizing composition of Example 2, the whole was stirred at ordinary temperature to effect complete dissolution, thereby an 8% PRB-containing pre-concentrate being obtained.

Example 11

After 500 μL of a 30 mg/mL ethanol solution of cyclosporin A (CyA) was added to 200 μL of the solubilizing composition of Example 2 and was completely dissolved therein, evaporation was conducted at about 50° C. to remove ethanol by distillation, thereby a 7.5% CyA-containing pre-concentrate being obtained.

Example 12

After 500 μL of a 20 mg/mL solution (ethanol:acetonitrile=1:1 (v/v)) of indomethacin (IND) was added to 200 μL of the solubilizing composition of Example 2 and was completely dissolved therein, evaporation was conducted at about 50° C. to remove ethanol and acetonitrile by distillation, thereby a 5% IND-containing pre-concentrate being obtained.

Example 13

After 500 μL of a 10 mg/mL ethanol solution of paclitaxel (PTX) was added to 200 μL of the solubilizing composition of Example 2 and was completely dissolved therein, evaporation was conducted at about 50° C. to remove ethanol by distillation, thereby a 2.5% PTX-containing pre-concentrate being obtained.

Example 14

After 500 μL of a 2 mg/mL solution (ethanol:acetonitrile=1:1 (v/v)) of methoxyprogesterone acetate (MPS) was added to 200 μL of the solubilizing composition of Example 2 and was completely dissolved therein, evaporation was conducted at about 50° C. to remove ethanol and acetonitrile by distillation, thereby a 0.5% MPS-containing pre-concentrate being obtained.

Example 15

After 500 μL of a 4 mg/mL solution (ethanol:acetonitrile=1:1 (v/v)) of mefenamic acid (MFA) was added to 200 μL of the solubilizing composition of Example 2 and was completely dissolved therein, evaporation was conducted at about 50° C. to remove ethanol and acetonitrile by distillation, thereby a 1% MFA-containing pre-concentrate being obtained.

Example 16

After 500 μL of a 30 mg/mL ethanol solution of clofibrate (CLF) was added to 200 μL of the solubilizing composition of Example 2 and was completely dissolved therein, evaporation was conducted at about 50° C. to remove ethanol by distillation, thereby a 7.5% CLF-containing pre-concentrate being obtained.

Example 17

After 500 μL of a 12 mg/mL solution (ethanol:acetonitrile=1:1 (v/v)) of nifedipine (NFD) was added to 200 μL of the solubilizing composition of Example 2 and was completely dissolved therein, evaporation was conducted at about 50° C. to remove ethanol and acetonitrile by distillation, thereby a 3% NFD-containing pre-concentrate being obtained.

Example 18

After 500 μL of a 20 mg/mL acetone solution of benzbromarone (BzB) was added to 200 μL of the solubilizing composition of Example 2 and was completely dissolved therein, evaporation was conducted at about 50° C. to remove acetone by distillation, thereby a 5% BzB-containing pre-concentrate being obtained.

Example 19

After 500 μL of a 2 mg/mL acetonitrile solution of chlormadinone (CLM) was added to 200 μL of the solubilizing composition of Example 2 and was completely dissolved therein, evaporation was conducted at about 50° C. to remove acetonitrile by distillation, thereby a 0.5% CLM-containing pre-concentrate being obtained.

With regard to the solubilizing compositions of Examples 10 to 19, evaluation of performance was conducted as in Examples 1 to 9. Results are shown in Table 8.

TABLE 8

|  | Example 10 | Example 11 | Example 12 | Example 13 | Example 14 | Example 15 | Example 16 | Example 17 | Example 18 | Example 19 |
|---|---|---|---|---|---|---|---|---|---|---|
| Hardly water-soluble medical agent | PRB | CyA | IND | PTX | MPS | MFA | CLF | NFD | BzB | CLM |
| Concentration of medical agent in pre-concentrate | 8% | 7.5% | 5% | 2.5% | 0.5% | 1% | 7.5% | 3% | 5% | 0.5% |
| Appearance of pre-concentrate |  |  |  |  |  |  |  |  |  |  |
| After preparation | ○ | ○ | ○ | ○ | ○ | ○ | ○ | ○ | ○ | ○ |
| After 1 day | ○ | ○ | ○ | ○ | ○ | ○ | ○ | ○ | ○ | ○ |
| Dispersion rate | A | A | A | A | A | A | A | A | A | A |
| Particle diameter (nm) | 26.1 | 25.7 | 17.1 | 25.1 | 30.9 | 23.5 | 30.9 | 41.4 | 27.1 | 12.3 |

With regard to the pre-concentrate of Example 10, an intestinal absorption test was conducted using rats. A commercially available probucol preparation (Lorelco tablet: Otsuka Pharmaceutical Co., Ltd.) was used as a control substance.

<Rat Intestinal Absorption Test (n=5)>

Animal used: Male SD rats (8 weeks old)

Administration method: With regard to Example 10 and the commercially available preparation, a drug solution of 20 mg/mL was prepared with purified water and was orally administered in an amount of 100 mg/kg.

Blood collection: Blood after the passage of 0, 2, 4, 6, or 8 hours from the administration was collected from coccygeal vein. The blood was immediately subjected to centrifugation to obtain blood serum.

Quantitative determination: The blood serum was subjected to protein removal and extraction by usual methods and then quantitative determination was conducted by HPLC.

Conditions for Quantitative Determination

Column: 5 μm Hypersil ODS (250 mm×4.6 mm, chemco, Japan)

Mobile phase: acetonitrile:hexane:0.1M ammonium acetate=180:13:7 (v/v)

Flow rate: 0.9 mL/min

Wavelength: 254 nm

With regard to Example 10 and the commercially available agent, change in blood concentration was shown in FIG. 1 and maximum blood concentration (Cmax) and area under concentration (AUC) were shown in Table 9.

TABLE 9

|  | Cmax (µg/mL) | AUC$_{0\to 8}$ (µg · h/mL) |
| --- | --- | --- |
| Example 10 | 0.834 ± 0.106 | 5.078 |
| Commercially available agent | 0.086 ± 0.051 | 0.519 |

Since the solubilizing composition of the invention satisfies all requirements that a medical agent can be contained in a high concentration, self-emulsification (self-microemulsification) is possible, a dispersion rate into water is high, and particle size after dispersion is small and is widely applicable to various hardly water-soluble medical agents, the composition is useful for improvement in intestinal absorbability and bioavailability of various kinds of hardly water-soluble medical agents. In addition, it is useful for solubilization of hardly water-soluble compounds for conducting various tests such as toxicity tests in the development of new drugs such as antimalignant drugs, immunosuppressive agents, antibiotics, antifungal agents, antihyperlipidemic agents, and antiinflammatory agents, wherein most of new-drug candidate substances are hardly water-soluble.

What is claimed is:

1. A solubilizing composition comprising (A) at least one oily component selected from the group consisting of esters of oleic acid with alcohols having 1 to 3 carbon atoms and triglycerides of fatty acids having 6 to 12 carbon atoms, (B) a polyoxyethylenesorbitan fatty acid ester, (C) a polyhydric alcohol which is liquid between 15° C. and 25° C., and (D) one or more acidic phospholipids wherein the fatty acid constituting an acyl group thereof is selected from the group consisting of saturated fatty acids having 6 to 14 carbon atoms and unsaturated fatty acids having 16 to 18 carbon atoms, wherein said composition comprises 20 to 40% by weight of the component (A), 30 to 45% by weight of the component (B), 15 to 40% by weight of the component (C), and 0.5 to 4% by weight of the component (D), based on 100% by weight of a total amount of the components (A) to (D), and wherein the amount of water in said solubilizing composition is 0.5% by weight or less with respect to the total weight of said solubilizing composition.

2. The solubilizing composition according to claim 1, wherein the solubilizing composition further comprises (E) ethanol in an amount of 0.1 to 10% by weight based on the total amount of the components (A) to (D).

3. The solubilizing composition according to claim 1, wherein the component (A) is selected from the group consisting of ethyl oleate and triglycerides of fatty acids having 8 to 10 carbon atoms.

4. The solubilizing composition according to claim 2, wherein the component (A) is selected from the group consisting of ethyl oleate and triglycerides of fatty acids having 8 to 10 carbon atoms.

5. The solubilizing composition according to claim 1, wherein the polyoxyethylenesorbitan fatty acid ester (B) is an ester of a fatty acid having 12 to 18 carbon atoms and an average addition mole number of the oxyethylene group is 15 to 25.

6. The solubilizing composition according to claim 2, wherein the polyoxyethylenesorbitan fatty acid ester (B) is an ester of a fatty acid having 12 to 18 carbon atoms and an average addition mole number of the oxyethylene group is 15 to 25.

7. The solubilizing composition according to claim 5, wherein the polyoxyethylenesorbitan fatty acid ester (B) is an ester of a fatty acid having 12 or 18 carbon atoms.

8. The solubilizing composition according to claim 6, wherein the polyoxyethylenesorbitan fatty acid ester (B) is an ester of a fatty acid having 12 or 18 carbon atoms.

9. The solubilizing composition according to claim 1, wherein the polyhydric alcohol (C) is propylene glycol or glycerin.

10. The solubilizing composition according to claim 2, wherein the polyhydric alcohol (C) is propylene glycol or glycerin.

11. The solubilizing composition according to claim 1, wherein the acidic phospholipid (D) is selected from the group consisting of phosphatidylglycerol, phosphatidylserine, and phosphatidic acid.

12. The solubilizing composition according to claim 2, wherein the (D) acidic phospholipid is selected from the group consisting of phosphatidylglycerol, phosphatidylserine, and phosphatidic acid.

13. The solubilizing composition according to claim 11, wherein the fatty acid constituting the acyl group of the acidic phospholipid (D) is selected from the group consisting of saturated fatty acids having 6 to 14 carbon atoms and oleic acid.

14. The solubilizing composition according to claim 12, wherein the fatty acid constituting the acyl group of the acidic phospholipid (D) is selected from the group consisting of saturated fatty acids having 6 to 14 carbon atoms and oleic acid.

15. A solubilizing pre-concentrate of a hardly water-soluble compound, which comprises the solubilizing composition according to claim 1 and the compound.

16. The pre-concentrate according to claim 15, wherein the solubilizing pre-concentrate is a pharmaceutical composition comprising the hardly water-soluble compound as an active component.

17. A solubilizing pre-concentrate of a hardly water-soluble compound, wherein the solubilizing pre-concentrate comprises the solubilizing composition according to claim 2 and the compound.

18. The pre-concentrate according to claim 17, which is a pharmaceutical composition comprising the hardly water-soluble compound as an active component.

* * * * *